United States Patent
Eldin

(10) Patent No.: US 6,200,461 B1
(45) Date of Patent: Mar. 13, 2001

(54) METHOD FOR INHIBITING POLYMERIZATION OF ETHYLENICALLY UNSATURATED HYDROCARBONS

(75) Inventor: Sherif Eldin, Houston, TX (US)

(73) Assignee: BetzDearborn Inc., Trevose, PA (US)

( * ) Notice: Subject to any disclaimer, the term of this patent is extended or adjusted under 35 U.S.C. 154(b) by 0 days.

(21) Appl. No.: 09/186,832

(22) Filed: Nov. 5, 1998

(51) Int. Cl.⁷ ..................................... C07C 7/20
(52) U.S. Cl. .................. 208/48 AA; 208/48 R; 585/950; 203/8; 203/9
(58) Field of Search ............... 208/48 R, 48 AA; 585/950; 203/8, 9

(56) References Cited

U.S. PATENT DOCUMENTS

| | | | |
|---|---|---|---|
| 2,399,340 | * | 4/1946 | Franz ........................... 203/9 |
| 2,510,847 | * | 6/1950 | Wilson ......................... 203/9 |
| 3,654,129 | * | 4/1972 | Bloch ........................... 208/48 |
| 4,439,278 | * | 3/1984 | Douglas et al. ............... 203/9 |
| 4,775,458 | * | 10/1988 | Forester ...................... 208/48 AA |
| 4,927,519 | * | 5/1990 | Forester ...................... 208/48 AA |
| 4,929,778 | * | 5/1990 | Roling ......................... 585/3 |
| 5,128,022 | * | 7/1992 | Reid ............................. 208/48 AA |
| 5,173,213 | * | 12/1992 | Miller et al. ................. 252/394 |
| 5,221,498 | * | 6/1993 | Reid et al. ................... 252/403 |
| 5,282,957 | * | 2/1994 | Wright et al. ................ 208/48 AA |
| 5,714,055 | * | 2/1998 | Lewis et al. ................. 208/48 R |

* cited by examiner

*Primary Examiner*—Walter D. Griffin
*Assistant Examiner*—Nadine Preisch
(74) *Attorney, Agent, or Firm*—Greenblum & Bernstein, P.L.C.

(57) ABSTRACT

Methods and compositions for inhibiting the polymerization of ethylenically unsaturated hydrocarbons are disclosed. Combinations of aminophenol compound and either of phenylenediamine or hydroxylamine compounds are effective at inhibiting this polymerization under both processing and storage conditions.

14 Claims, No Drawings

METHOD FOR INHIBITING POLYMERIZATION OF ETHYLENICALLY UNSATURATED HYDROCARBONS

FIELD OF THE INVENTION

The present invention provides for methods and compositions for inhibiting the polymerization of ethylenically unsaturated hydrocarbons, such as olefins and diolefins.

BACKGROUND OF THE INVENTION

Common industrial methods for producing ethylenically unsaturated monomers include a variety of purification processes such as distillation to remove impurities. Purification operations are often carried out at elevated temperatures and this can increase the rate of undesired polymerization. Polymerization, such as thermal polymerization, during the monomer purification process, results not only in loss of desired monomer end-product, but also in production efficiency caused by polymer formation and agglomeration on process equipment. In heat requiring operations, such agglomeration adversely affects heat transfer efficiency.

Typically the monomers are stabilized with the addition of substances which will act as inhibitors or retarders of polymerization.

Certain ethylenically unsaturated monomers such as the diolefins butadiene and isoprene will polymerize when left in storage tanks and during transportation at temperatures as low as room temperature. This polymerization is initiated by reaction of the diolefin monomer with oxygen present in the monomer containing system. This reaction will form peroxides and free radical species which will perpetuate the reaction with the diolefin monomer.

Various approaches have been attempted with regard to this problem of polymerization. U.S. Pat. No. 3,148,225 teaches that N,N-dialkylhydroxylamines will inhibit the polymerization of popcorn polymer formation in olefin monomer recovery systems. In comparative studies, p-aminophenol was less effective than the hydroxylamines at inhibiting popcorn polymer formation. U.S. Pat. No. 3,342,723 tests p- and o-aminophenols for inhibiting fouling of hydrocarbon liquids. These compounds proved effective at inhibiting the formation and adhesion of coke-like deposits during refinery operations. o-phenylenediamine was also demonstrated to be effective in the oil refining apparatus.

U.S. Pat. No. 5,510,547 teaches that a combination of a phenylenediamine compound and a hydroxylamine compound is effective as inhibiting the polymerization of vinyl aromatic monomers during processing conditions. U.S. Pat. No. 4,720,566 teaches that a combination of a hydroxylamine and a phenylenediamine compound is effective at inhibiting the polymerization of acrylonitrile during its production.

DETAILED DESCRIPTION OF THE INVENTION

The present invention provides for methods and compositions for inhibiting the polymerization of ethylenically unsaturated hydrocarbons comprising adding an effective inhibiting amount of a composition comprising an aminophenol compound and at least one of a phenylenediamine compound and a hydroxylamine compound "(Aminophenol compositions")."

The ethylenically unsaturated monomers are characterized as polymerizable ethylenically unsaturated hydrocarbons and include olefins and diolefins. The olefins contain about 2 to about 20 carbon atoms, preferably 2 to 8 carbon atoms and the diolefins are conjugated and contain about 2 to about 20 carbon atoms with 4 to 6 carbon atoms preferred. Examples of these compounds include ethylene dichloride, ethylene glycol, aromatics from ethylene plants and pyrolysis gasoline.

The aminophenol compounds generally have the formula:

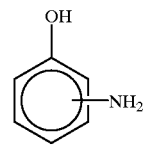

where the amino group can be ortho, meta or para to the hydroxyl group. Preferably, the o-aminophenol is preferred.

The phenylenediamine compounds useful in the present invention generally have the formula:

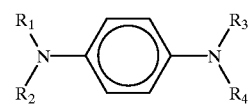

wherein $R_1$, $R_2$, $R_3$ and $R_4$ are the same or different and are hydrogen, alkyl, aryl, alkaryl or aralkyl groups having about 1 to about 20 carbon atoms. Preferably the phenylenediamine compound is selected from the group consisting of N,N'-bis-di-sec-butyl-p-phenylenediamine and N-phenyl-N'-(1,4-dimethylpentyl)-p-phenylenediamine.

The hydroxylamine compounds useful in the present invention generally have the formula:

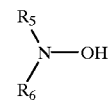

wherein $R_5$ and $R_6$ are the same or different and are hydrogen, alkyl, aryl, alkaryl, aralkyl or hydroxyalkyl groups and have about three to about twenty carbon atoms. The preferred hydroxylamine compounds are selected from the group consisting of N, N'-diethylhydroxylamine (DEHA) and bis-N, N'-(hydroxypropyl-hydroxylamine) (HPHA).

The aminophenol compositions of the present invention are effective at inhibiting the polymerization of ethylenically unsaturated monomers during both storage and processing conditions. Storage conditions also include transportation of the monomers. These conditions will usually have oxygen present and can be at elevated temperatures of up to 100° C. The processing conditions are usually distillation and purification processes and are run at elevated temperatures of 95° and 125° C. where oxygen can be present or absent.

For purposes of the present invention, the term "effective amount for the purpose" is that amount of aminophenol compositions necessary to inhibit polymerization of the ethylenically unsaturated monomers. This amount will vary according to the conditions under which the monomers are subjected during the storage and/or handling thereof. During processing, for example, high temperatures and higher monomers contamination will require larger amounts of the aminophenol compositions.

Preferably, the total amount of the aminophenol compositions added to the ethylenically unsaturated monomer will range from about 1 part to about 10,000 parts per million parts of monomer. More preferably, the aminophenol compositions are added at a range of about 1 part to about 100 parts per million parts monomer.

The weight ratios of aminophenol compound to the other compounds present in the aminophenol compositions is presented in Table A below.

TABLE A

|  | Aminophenol Compound |
|---|---|
| Phenylenediamine Compound | 1:9 to 9:1 |
| Hydroxylamine Compound | 1:9 to 9:1 |

Accordingly, it is possible to produce a more effective vinyl aromatic monomer polymerization inhibition treatment than is obtainable by the use of one ingredient alone when measured at comparable treatment levels. This enhanced activity will allow for the concentration of each of these ingredients to be lowered and the total quantity of polymerization inhibitor particularly at higher processing temperatures may be reduced.

The aminophenol compositions of the present invention may be added to the ethylenically unsaturated hydrocarbon as either a dispersion or as a solution using a suitable liquid carrier or solvent. Any solvent that is compatible with the individual ingredients and with the monomer may be employed.

The aminophenol compositions may be added to the ethylenically unsaturated hydrocarbon vinyl aromatic by any conventional method, either as individual components or as a combination of components. It is preferred that the ingredients be added to the monomer as a single treatment.

This invention will now be further described with reference to a number of specific examples which are to be regarded solely as illustrative and not as restricting the scope of the invention.

EXAMPLES

20% uninhibited isoprene in heptane was placed in a pressure vessel. This mixture was then purged once with nitrogen before placing it under 100 psi nitrogen. The pressure vessel was then placed in a 100° C. water bath for 4 hours allowing polymerization of the diolefin. The mixture was then allowed to cool at room temperature. The sample was evaporated and the remaining gums/polymer weight was obtained.

The chemicals employed in the testing are summarized in Table B.

TABLE B

| o-AP | ortho-aminophenol |
| DEHA | N, N'-diethylhydroxylamine |
| PDA I | N, N'-bis-di-sec-butyl-p-phenylenediamine |
| PDA II | N-phenyl-N'-(1,4-dimethylpentyl)-p-phenylenediamine |

The results of this testing for a combination of aminophenol compound and phenylenediamine are presented in Table I.

TABLE I

Heat Induced Gum Test

| Treatment | Total ($\mu$ Moles) | Gums (mg/100 ml) |
|---|---|---|
| o-AP | 1.1 | 52 |
| DEHA | 1.1 | 50 |
| PDA I | 1.1 | 6 |
| o-AP/DEHA (1:1) | 1.1 | 16 |
| o-AP/PDA I (1:1) | 1.1 | 0.4 |

These results demonstrate that the combination of an aminophenol compound and either a hydroxylamine compound or a phenylenediamine compound was more effective than the particular individual component.

The concentration of the individual components was lowered by half, but the ratio between two component treatments was kept equimolar in the next study. These results are presented in Table II.

TABLE II

| Treatment | Total ($\mu$ Moles) | Gums (mg/100 ml) |
|---|---|---|
| o-AP | 0.55 | 59 |
| DEHA | 0.55 | 102 |
| PDA I | 0.55 | 32 |
| o-AP/DEHA (1:1) | 0.55 | 54 |
| o-AP/PDA I (1:1) | 0.55 | 16 |

These results also demonstrate that the combination of an aminophenol compound with either a hydroxylamine compound or a phenylenediamine compound is more effective at inhibiting polymerization than the individual components.

Additional studies were performed using the same components, but with a constant final dosage. These results are presented in Table III.

TABLE III

Heat Induced Gum Test

| Treatment | Total (ppm) | Gums (mg/100 ml) |
|---|---|---|
| o-AP | 2 | 46 |
| DEHA | 2 | 55 |
| PDA I | 2 | 64 |
| PDA II | 2 | 45 |
| o-AP/DEHA (1:1) | 2 | 21 |
| o-AP/PDA I (1:1) | 2 | 34 |
| o-AP/PDA II (1:1) | 2 | 35 |
| o-AP/DEHA/PDA I (1:1:1) | 2 | 11 |

These test results not only demonstrate the enhanced activity occasioned by use of the combination of aminophenol compound with either a phenylenediamine or a hydroxylamine compound, but also the excellent results occasioned by use of all three compounds together.

Further testing was performed with DEHA and o-AP at a constant dosage of 1 ppm. These results are presented in Table IV.

TABLE IV

Heat Induced Gum Test

| o-AP(%) | DEHA (%) | Gums (mg/100 ml) |
|---|---|---|
| 100 | 0 | 51 |
| 75 | 25 | 45 |

TABLE IV-continued

Heat Induced Gum Test

| o-AP(%) | DEHA (%) | Gums (mg/100 ml) |
|---|---|---|
| 67 | 33 | 46 |
| 50 | 50 | 31 |
| 33 | 67 | 38 |
| 25 | 75 | 47 |
| 0 | 100 | 81 |

These results demonstrate the synergy between C-AP and DEHA at inhibiting ethylenically unsaturated hydrocarbon polymerization.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of ethylenically unsaturated hydrocarbons comprising adding to said hydrocarbons an effective inhibiting amount of a composition comprising aminophenol compound and at least one of phenylenediamine compound and hydroxylamine compound.

2. The method as claimed in claim 1 wherein said aminophenol compound comprises at least one of para-aminophenol, meta-aminophenol and ortho-aminophenol.

3. The method as claimed in claim 1 wherein said phenylenediamine compound has the formula:

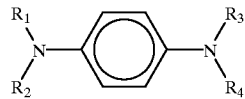

wherein $R_1$, $R_2$, $R_3$ and $R_4$ are the same or different and are hydrogen, alkyl, aryl, alkaryl, and aralkyl having about 1 to about 20 carbon atoms.

4. The method as claimed in claim 1 wherein said hydroxylamine compound has the formula:

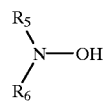

wherein $R_5$ and $R_6$ are the same or different and are hydrogen, alkyl, aryl, alkaryl, aralkyl or hydroxyalkyl groups and have about three to about twenty carbon atoms.

5. The method as claimed in claim 2 wherein said aminophenol compound is ortho-aminophenol.

6. The method as claimed in claim 3 wherein said phenylenediamine compound comprises at least one of N,N'-bis-di-sec-butyl-p-phenylenediamine and N-phenyl-N'-(1,4-dimethylpentyl)-p-phenylenediamine.

7. The method as claimed in claim 4 wherein said hydroxylamine compound comprises at least one of N,N'-diethylhydroxylamine and bis-N,N'-(hydroxypropyl-hydroxylamine).

8. The method as claimed in claim 1 wherein said ethylenically unsaturated hydrocarbons are undergoing processing.

9. The method as claimed in claim 1 wherein said ethylenically unsaturated hydrocarbons are in storage conditions.

10. The method as claimed in claim 1 wherein said ethylenically unsaturated hydrocarbons undergo processing at temperatures of about 95° to about 125° C.

11. The method as claimed in claim 1 wherein said ethylenically unsaturated hydrocarbons comprise at least one of olefins and diolefins.

12. The method as claimed in claim 11 wherein said olefins and said diolefins contain about 2 to about 20 carbons.

13. The method as claimed in claim 1 wherein said composition is added to said hydrocarbons in an amount ranging from about 1 to about 10,000 parts per million parts of hydrocarbons.

14. The method as claimed in claim 1 wherein the weight ratio of aminophenol compound to either of said phenylenediamine compound and hydroxylamine compound ranges from about 1:9 to about 9:1.

* * * * *